United States Patent [19]
Sarr

[11] Patent Number: 4,799,167
[45] Date of Patent: Jan. 17, 1989

[54] ULTRASONIC 64 CHANNEL INSPECTION SYSTEM WITH MULTIGATE/MULTIMODE SELECTION SOFTWARE CONFIGURABILITY

[75] Inventor: Dennis P. Sarr, Kent, Wash.

[73] Assignee: The Boeing Company, Del.

[21] Appl. No.: 815,044

[22] Filed: Dec. 31, 1985

[51] Int. Cl.⁴ ............................................. G01N 29/04
[52] U.S. Cl. ..................... 364/507; 73/612; 73/610
[58] Field of Search ............... 364/506, 507, 550, 570; 73/624, 625, 628, 644, 619, 610, 611, 612

[56] References Cited

U.S. PATENT DOCUMENTS

| | | | |
|---|---|---|---|
| 3,792,613 | 2/1974 | Couture | 73/67.9 |
| 3,857,052 | 12/1974 | Beller | 340/149 R |
| 3,875,381 | 4/1975 | Wingfield et al. | 235/151.3 |
| 3,896,662 | 7/1975 | Camp et al. | 73/67.8 S |
| 3,958,451 | 5/1976 | Richardson | 73/67.8 S |
| 4,012,952 | 3/1977 | Dory | 73/67.7 |
| 4,070,905 | 1/1978 | Kossoff | 73/614 |
| 4,150,577 | 4/1979 | Fetheroff | 73/611 |
| 4,160,386 | 7/1979 | Jackson et al. | 73/625 |
| 4,173,007 | 10/1979 | McKeighen et al. | 367/11 |
| 4,173,898 | 11/1979 | Förstermann et al. | 73/611 |
| 4,229,796 | 10/1980 | Garrett | 364/507 |
| 4,261,040 | 6/1979 | Weidman et al. | 364/554 |
| 4,354,388 | 10/1982 | Diepers et al. | 73/612 |
| 4,373,395 | 2/1983 | Borburgh | 73/607 |
| 4,448,076 | 5/1984 | van Heelsbergen | 73/628 |
| 4,456,982 | 6/1984 | Tournois | 73/624 |

Primary Examiner—Parshotam S. Lall
Assistant Examiner—V. N. Trans
Attorney, Agent, or Firm—Finnegan, Henderson, Farabow, Garrett & Dunner

[57] ABSTRACT

Nondestructive ultrasonic testing systems and methods include data processing capabilities which allow time division multiplexing of several transducer channels by a smaller number of gates for signal processing, and time division multiplexing the outputs of the gates for subsequent evaluation.

22 Claims, 10 Drawing Sheets

| CHANNEL | SBCX11 | SBCX12 | DISP | DISPA |
|---|---|---|---|---|
| 1 | 06 | FF | D7 | 06 |
| . | | | | |
| . | | | | |
| . | | | | |
| 21 | 06 | FF | D7 | 06 |
| 22 | 0D | FF | D7 | 07 |
| 23 | 13 | FF | D7 | 08 |
| 24 | 13 | FF | D7 | 08 |
| 25 | 13 | FF | D7 | 08 |
| 26 | 13 | FF | D7 | 08 |
| 27 | 0D | FF | D7 | 07 |
| 28 | 0D | FF | D7 | 07 |
| 29 | 0D | FF | D7 | 07 |
| 30 | 0D | FF | D7 | 07 |
| 31 | 0D | FF | D7 | 07 |
| 32 | 0D | FF | D7 | 07 |
| 33 | FF | 23 | 6B | 85 |
| 34 | FF | 23 | 6B | 85 |
| 35 | FF | 06 | 6E | 83 |
| 36 | FF | 06 | 6E | 83 |
| 37 | FF | 06 | 6E | 83 |
| 38 | FF | 06 | 6E | 83 |
| 39 | FF | 0D | 6D | 84 |
| . | | | | |
| . | | | | |
| . | | | | |
| 64 | FF | 0D | 6D | 84 |

ALL VALUES ARE HEXADECIMAL

FIG. 7.

| CHANNEL | SBCX11 | SBCX12 | DISP | DISPA |
|---|---|---|---|---|
| 1 | 06 | FF | D7 | 06 |
| . | | | | |
| . | | | | |
| 21 | 06 | FF | D7 | 06 |
| 22 | 0D | FF | D7 | 07 |
| 23 | 13 | FF | D7 | 08 |
| 24 | 13 | FF | D7 | 08 |
| 25 | 13 | FF | D7 | 08 |
| 26 | 13 | FF | D7 | 08 |
| 27 | 0D | FF | D7 | 07 |
| 28 | 0D | FF | D7 | 07 |
| 29 | 0D | FF | D7 | 07 |
| 30 | 0D | FF | D7 | 07 |
| 31 | 0D | FF | D7 | 07 |
| 32 | 0D | FF | D7 | 07 |
| 33 | FF | 23 | 6B | 85 |
| 34 | FF | 2B | 6B | 85 |
| 35 | FF | 0D | 6D | 84 |
| 36 | FF | 15 | 6D | 84 |
| 37 | FF | 0D | 6D | 84 |
| 38 | FF | 15 | 6D | 84 |
| 39 | FF | 06 | 6E | 83 |
| . | | | | |
| . | | | | |
| 64 | FF | 06 | 6E | 83 |

ALL VALUES ARE HEXADECIMAL

*FIG. 8.*

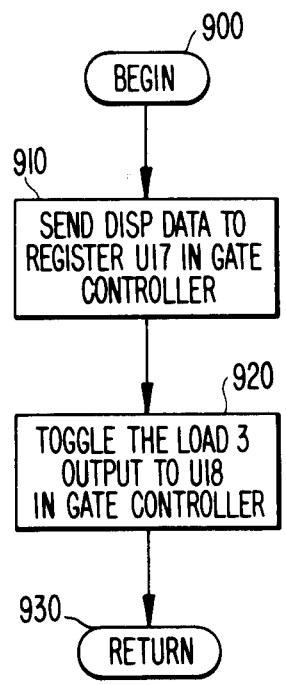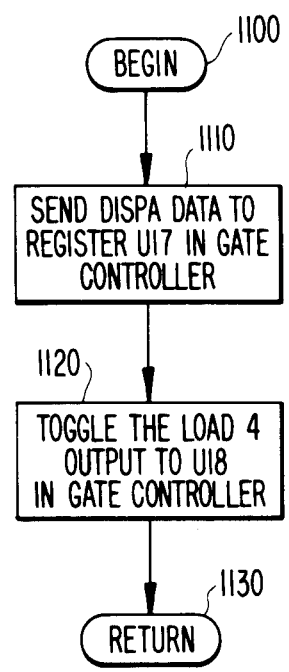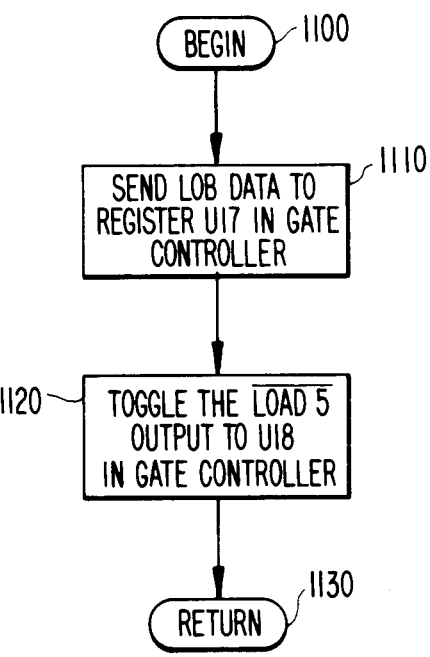

ULTRASONIC 64 CHANNEL INSPECTION SYSTEM WITH MULTIGATE/MULTIMODE SELECTION SOFTWARE CONFIGURABILITY

CROSS REFERENCE TO RELATED APPLICATIONS

The invention is related to the following copending U.S. patent applications assigned to the assignee of the present invention:

DATA RECORDING APPARATUS FOR AN ULTRASONIC INSPECTION SYSTEM, Ser. No. 06/815,050, filed Dec. 31, 1985 by D. P. Sarr, allowed;

ULTRASONIC INSPECTION SYSTEM WITH LINEAR TRANSDUCER ARRAY, Ser. No. 06/815,047, filed on Dec. 31, 1985 by D. P. Sarr and F. D. Young, allowed;

ULTRASONIC INSPECTION SYSTEM APPARATUS AND METHOD, Ser. No. 06/815,048, filed on Dec. 31, 1985 by D. P. Sarr, allowed;

ULTRASONIC INSTRUMENTATION FOR EXAMINATION OF VARIABLE-THICKNESS OBJECTS, Ser. No. 06/815,038, filed on Dec. 31, 1985 by D. P. Sarr, allowed;

AN IMPROVED ULTRASONIC TESTING APPARATUS, Ser. No. 06/815,163, filed Dec. 31, 1985 by G. A. Geithman and D. P. Sarr, allowed; and ULTRASONIC TRANSDUCER WITH SHAPED BEAM INTENSITY PROFILE, Ser. No. 06/815,162, filed Dec. 31, 1985 by G. A. Geithman and D. H. Gilbert, now U.S. Pat. No. 4,700,575.

BACKGROUND OF THE INVENTION

The present invention relates to field of non-destructive ultrasonic testing and, more particularly, to devices used to control such testing.

Because of their lighter weight, composite materials, such as epoxy resins, are replacing aluminum as material for use in manufacturing aircraft parts and other equipment. Parts made of such composite materials, however, require careful inspection before installation in an aircraft. Ultrasonics is a widely used method of nondestructive inspection of such parts.

Because every portion of a part must be examined, ultrasonic inspection systems require a large number of transducers in order to keep the inspection time per unit at an acceptable value. Depending on the part being inspected, different modes of ultrasonic inspection may be required. For example, with through transmission ultrasonics (TTU), one transducer transmits ultrasonic energy through a part and another transducer receives and converts the portion of that energy that is not reflected by the part. If there is no defect in the interior of the part, then the magnitude of ultrasonic energy received in a time window corresponding to the part thickness will exceed a preset threshold value. If the magnitude of the received energy is too low, then a defect was present in the interior of the part.

Another ultrasonic inspection mode is the pulse echo (PE) technique. For this technique, a single transducer both transmits ultrasonic energy to the part under test and receives reflections of that energy from the part. By examining the magnitude of reflections during a time period when reflections from the interior of the part under investigation are received (i.e., a time window), one can determine whether there is a reflection defect (a reflection magnitude above a threshold), or whether there is no defect (a reflection magnitude below the threshold).

A variation on the PE mode is the loss-of-back (LOB) mode. As in the PE mode, the LOB mode uses a single transducer to transmit and receive ultrasonic energy. In this case, however, the time window is set to receive reflections from the rear surface. When defects are present in the interior of the part they reflect much of the ultrasonic energy, causing the magnitude of the reflections from the rear surface to be below a threshold. The LOB detecting apparatus thus indicates the presence of a defect. By the same token, if the magnitude of rear surface reflections exceeds the threshold, then the LOB detecting apparatus indicates no defects.

In conventional ultrasonic control systems, each transducer channel requires a separate gate for processing. As used in this specification, a "transducer channel" refers to a single transmission path to and from one or more transducers which cooperate with each other in ultrasonic detection. For example, in the PE or LOB modes, a transducer channel would correspond to a single transducer, whereas in the TTU mode, a transducer channel would correspond to both the transmitting and receiving transducers. The term "gate" as used in this specification specifies a subsystem which processes ultrasonic signals received via a transducer channel. For example, TTU, PE or LOB gates process the corresponding ultrasonic signals in accordance with the TTU, PE, or LOB modes, respectively.

Conventional ultrasonic testing systems require a gate for each channel, and are thus not only very complex, but become very large and expensive when several transducers are used, such as in testing large and complicated aircraft parts. Furthermore, conventional systems require a complete reconfiguration when the ultrasonic testing requirements change.

One object of this invention is to simplify ultrasonic testing equipment by allowing relatively few gates to service several transducer channels.

Another object of this invention is a simple and relatively inexpensive means of reconfiguring an ultrasonic test system.

Additional objects and advantages of the present invention will be set forth in part in the description which follows and in part will be obvious from that description or may be learned by the practice of the invention. The objects and advantages of the invention may be realized and attained by the methods and apparatus defined in the appended claims.

SUMMARY OF THE INVENTION

The present invention overcomes the problems of the prior art and achieves the objects listed above by time-division-multiplexing the outputs of several channels for a single gate, and by controlling the interconnections between the gates and channels, and the signal processing by circuitry software rather than hardware.

In particular, to achieve the objects and in accordance with the purpose of the invention, as embodied and broadly described in the specification, the system for nondestructive ultrasonic testing of an object according to this invention comprises a plurality of transducer systems positioned proximate the object to transmit ultrasonic eneryy toward the object in response to activation signals, and to receive ultrasonic energy from the object and create investigation signals from that received energy. This system also comprises a pluality of channel switching systems coupled to the transducer systems to receive the investigation signals from the transducer systems and to output the activation signals to the transducer systems, the channel switching systems each including a set of input ports receiving pulse command and control signals; a set of output ports containing gate signals; means, coupled to the input ports and to the transducer systems, for transforming the pulse commands signals at the input ports into activation signals to drive the transducer systems; and means, coupled to the transducer systems and to the output ports, for selecting certain ones of the investigation signals from the transducer systems to be gate signals in accordance with the control signals, and for routing the gate signals to the output ports.

The system of this invention for nondestructive ultrasonic testing of an object also comprises gate signal processing electronics coupled to the output ports of the channel switching system to receive the gate signals, that electronics also having a command input port for receiving processing commands and a data processing output port. The gate signal processing electronics of this invention includes means for processing the gate signals to obtain defect information and means for selecting certain of the defect information according to the processing commands at the command input port, tee selected defect information being sent to the data processing output port. In addition, the system of invention includes data processing means, coupled to the data processing output port and to the channel switching input ports, for generating the pulse command signals and processing commands and for receiving and evaluating the selected defect information.

A method of nondestructive ultrasonic testing of an object according to this invention includes the steps of sending ultrasonic energy to an receiving ultrasonic energy from the object; transducing the received ultrasonic energy to form a channel signals; selecting certain of the channels signals to be gate signals; processing the gate signals to obtain defect information; and selecting certain of the defect information for subsequent processing.

The accompanying drawings, which are incorporated in and constitute a part of the specification, illustrate an embodiment of the invention and, together with the description, explain the principles of the invention.

BRIEF DESCRIPTION OF THE DRAWINGS

FIGS. 7 and 8 are two examples of a channel table, stored in the memory of the computer shown in FIG. 4, used for controlling the system of this invention;

FIGS. 9-14 are a flow charts showing system configuration operations of this invention.

DESCRIPTION OF THE PREFERRED EMBODIMENT

Reference will now be made in detail to a presently preferred embodiment of this invention, an example of which is illustrated in the accompanying drawings.

Figure 1:
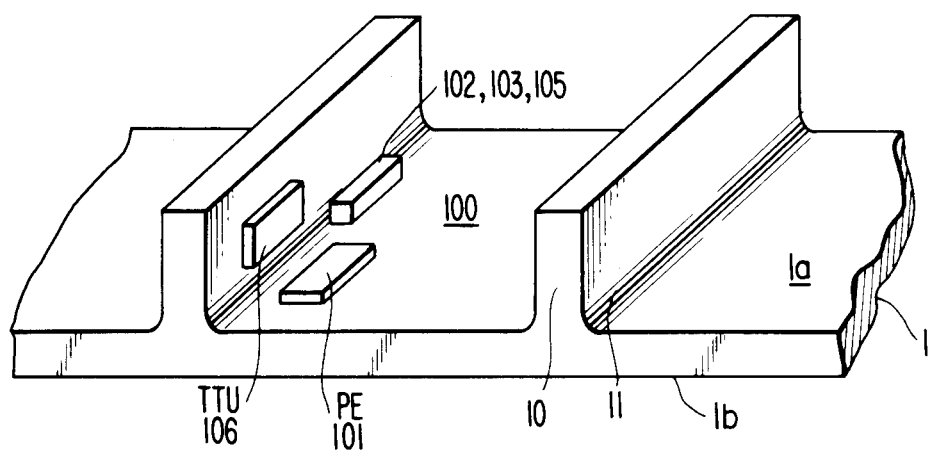
FIG. 1 depicts an exemplary object to be examined using the system and methods of this invention.

FIG. 1 shows an example of an object 1, made of composite material, to be examined using the ultrasonic detecting systems and methods of this invention. Object 1 is a sheet having an upper side 1a and lower side 1b. Lower side 1b is usually referred to as the "tool side" and upper side 1a is usually referred to as the "blade side."

To have adequate strength, sheets of composite material have ribs or blades, such as blade 10, which are typically parallel to each other and extend at right angles to the sheet. The point of attachment between a blade and the sheet is sometimes called a "radius" or a "fillet," such as fillet 11 in FIG. 1. Testing of object 1 requires an examination of the sheet as well as an examination of the fillets.

Figure 2:
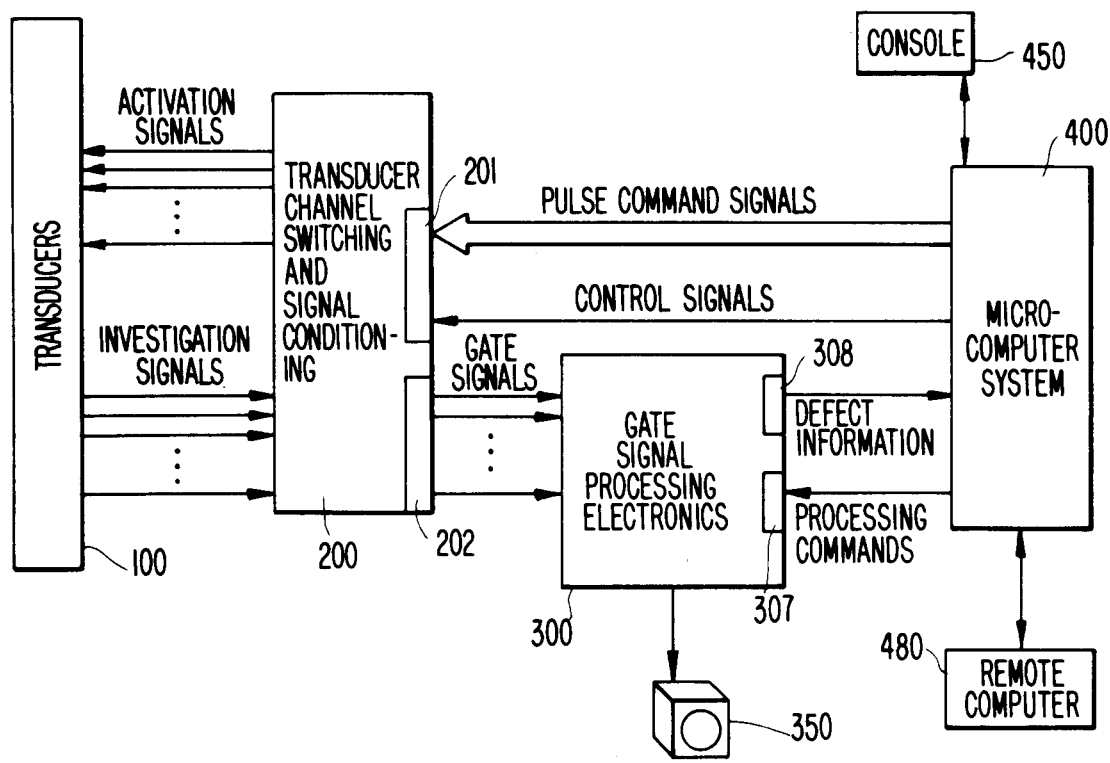
FIG. 2 is a block diagram of an embodiment of this invention.
Figure 3:
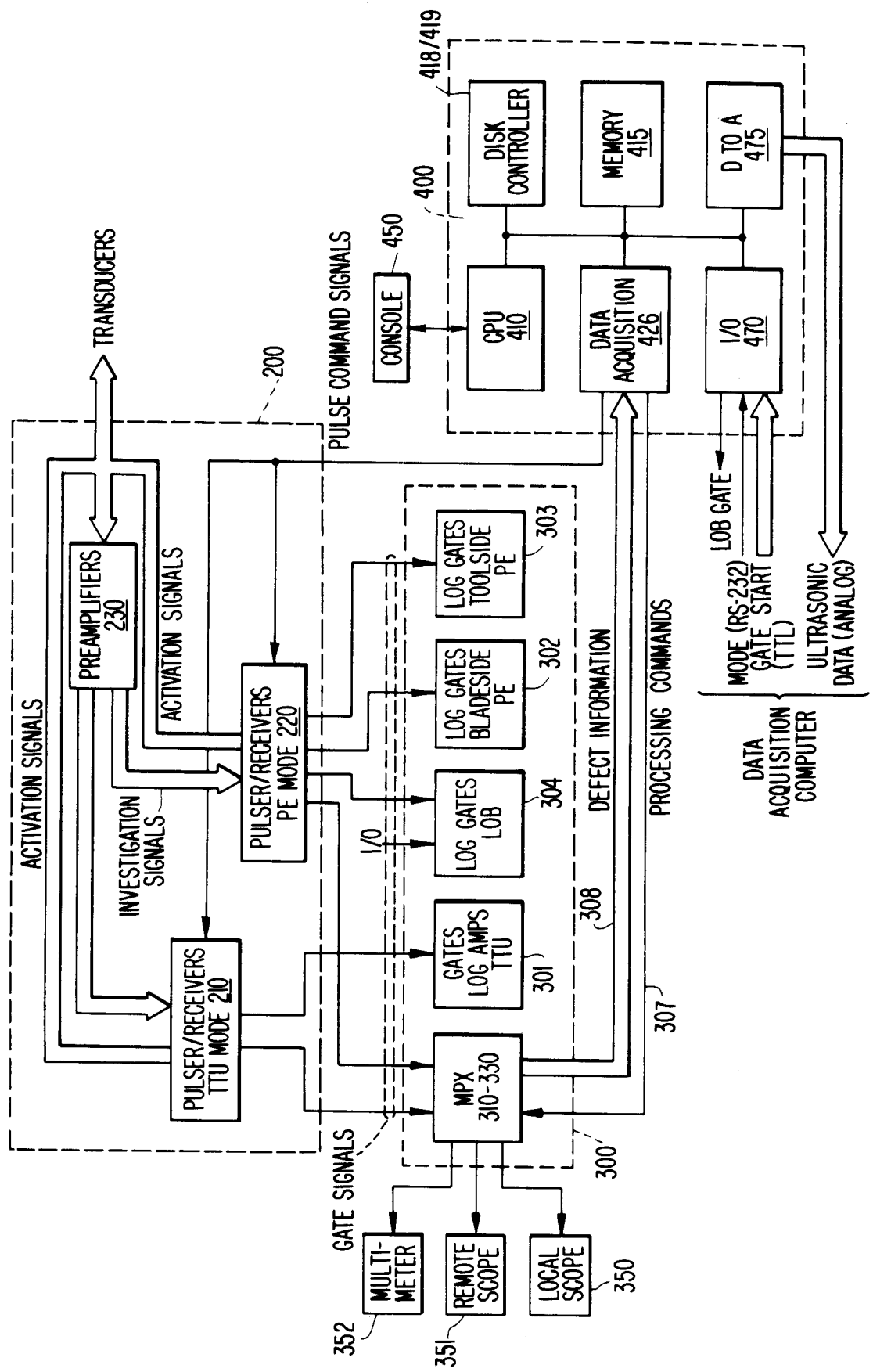
FIG. 3 shows a system diagram of the embodiment in FIG. 2.
Figure 4:
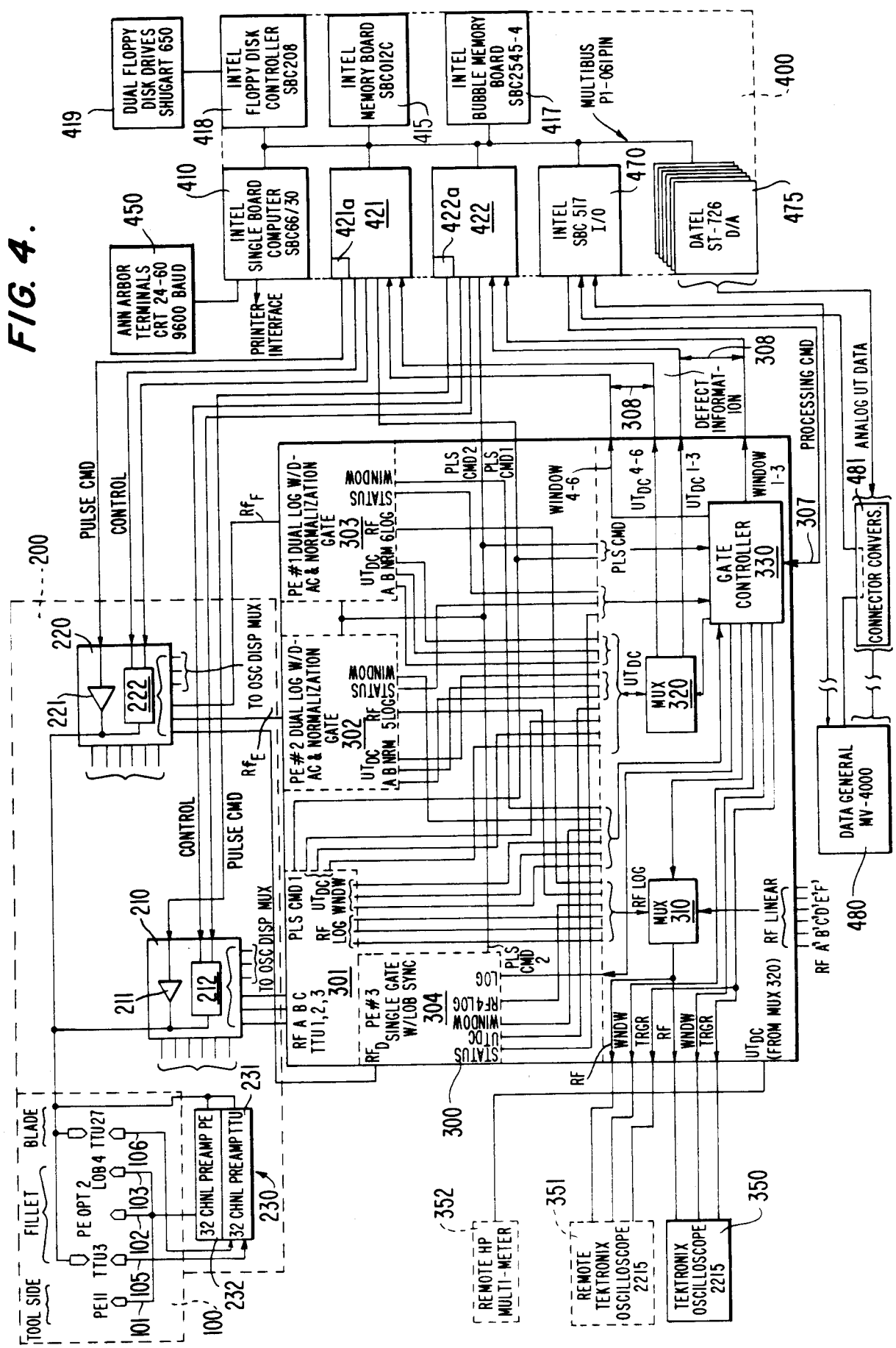
FIG. 4 shows a more detailed diagram of the system elements shown in the diagram in FIG. 3.

In the following description of the nondestructive ultrasonic testing system and apparatus of this invention, the same reference numerals in different drawings refer to like or equivalent system elements. FIG. 2 shows a block diagram of one embodiment of this invention and FIG. 3 shows a system diagram corresponding to that block diagram. FIG. 4 shows the system elements in FIG. 3 in more detail.

The present invention includes a plurality of transducer systems, such as transducers 100 in FIGS. 2 and 4, positioned proximate an object under test. In the preferred embodiment, there are thirty (30) sets of transducers for use in the TTU mode and seventeen (17) transducers for use in the PE or LOB mode. Eleven (11) of the transducers for use in the PE mode are denoted 101 and are used for examining the tool side of object 1. Two (2) of the transducers for use in the PE mode (which are optional) are denoted 102 and are used for examining the fillet. Four (4) of the seventeen transducers are denoted 103 and are used for examining the fillet in the LOB mode. Twenty-seven (27) of the transducers for use in the TTU mode are denoted 106 and are used for examining the blade, and the other three (3) TTU mode transducers are used for examining the fillet and are denoted 105. FIG. 1 shows a preferred placement of transducers 101-103, 105 and 106. Of course, some of the TTU mode transducers cannot be viewed due to the perspective shown in FIG. 1.

The system as configured in FIGS. 2-4 can handle up to 64 channels, although only 47 are used in the preferred embodiment shown. As will become apparent from the following explanation of this invention, the reconfiguration of this system, with the same or different numbers of transducer systems and channels, can be effected rather easily with this invention.

Transducers 100 transmit ultrasonic energy toward the object under investigation in response to activation signals, and receive ultrasonic energy from the object, the received energy being converted to investigation signals. The received energy can either be the reflected ultrasonic energy, as in the PE or LOB modes, or the non-reflected ultrasonic energy as in the TTU mode.

In accordance with the present invention, there is also a channel switching system coupled to the transducer systems to receive the investigation signals from and to send activation signals to those transducer systems. FIG. 2 shows a transducer channel switching and signal conditioning element 200 which provides these functions.

The channel switching system according to this invention includes a set of input ports and output ports shown in FIG. 2 as elements 201 and 202, respectively. The input ports 201 receive pulse command signals and control signals generated by microcomputer system 400. Output ports 202 output gate signals to gate signal processing electronics 300.

The channel switching system of the ultrasonic testing system of this invention includes means, coupled to the input ports and to the transducer systems, for transforming the pulse command signals at the input ports into activation signals to drive the transducer systems. Preferably, such transforming means includes a plurality of buffers for transforming pulse command signals, typically at standard TTL levels, into activation signals at high voltage levels. Examples of such buffers are elements 211 and 221, shown in FIG. 4 as part of a pair of pulser/receivers 210 and 220, respectively. The activation signals drive the corresponding transducers.

Figure 5:
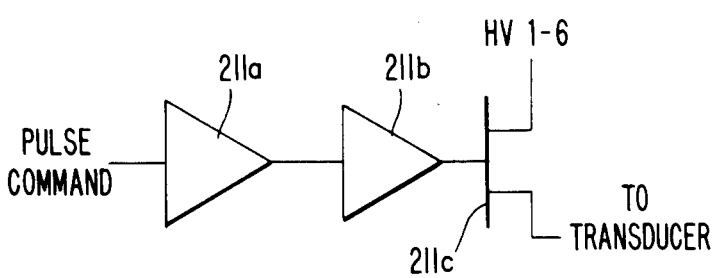
FIG. 5 shows a detailed diagram of a buffer in the system shown in FIG. 4.

FIG. 5 shows an example of part of one buffer 211 (or buffer 221) in greater detail. Preferably buffers 211 and 221 have similar construction. Buffer 211 includes a TTL buffer 211a which receives the pulse command signal and sends that signal to an MOS/FET driver 211b. Driver 211b then controls an MOS/FET high voltage transitor switch 211c to drive the transducer. The MOS/FET high voltage transitor switch is coupled to one of six high voltage sources HV1-6, High voltages sources HV1-6 are connected to transistor switch 211c either manually, e.q., by patching before operation, or automatically, e.g., using a transistor or relay switch.

The channel switching system of the nondestructive ultrasonic testing system of the present invention also includes means, coupled to the transducer systems and to the output ports, for selecting, in accordance with the control signals, certain ones of the investigation signals from the transducer systems to be gate signals, and for routing the gate signals to the output ports. In the preferred embodiment, such means may include channel multiplexers 212 and 222 in pulser/receivers 210 and 220, respectively, as shown in FIG. 4. Multiplexers 212 and 222 each have several investigation signals as inputs and each selects three gate signals as outputs: $Rf_A$, $Rf_B$, and $Rf_C$ for multiplexer 212 and $Rf_D$, $Rf_E$, and $Rf_F$ for multiplexer 222. In addition, multiplexers 212 and 222 produce a redundant set of outputs corresponding to gate signals $Rf_A$-$Rf_F$, for oscilloscope display purposes. Preferably, multiplexers 212 and 222 include standard analog multiplexers, such as elements DG506A manufactured by Siliconix, Inc.

Preferably, channel multiplexers 212 and 222 each include three sets of analog multiplexers to select as gate signals signals from three of the up to thirty-two (32) transducer channels. Each gate signal corresponds to a different gate, as described below. The selection occurs according to control signals from a microcomputer system 400 (FIGS. 2-4). The control signals include five-bit address lines for each multiplexer. By controlling those address lines, the time division multiplexing described below can be effected, and in the preferred embodiment of the invention, the sixty-four possible channels (or forty-seven active transducer channels) can be processed using only six gates.

In the preferred embodiment, each of the six gate signals corresponds to a different gate. Three of the gates are coupled to the TTU pulser/receiver and three of the gates are coupled to the PE and LOB pulser/receiver. Of course, other configurations may also be used, for example with greater or fewer channels per gate, or with a different arrangement of channels and gates.

Prior to being inputted to multiplexers 212 and 222, the investigation signals preferably pass through preamplifiers so that the levels of those signals are increased sufficiently for use with subsequent processing. In accordance with the preferred embodiment shown in FIGS. 3 and 4, preamplifier 230 serves this purpose. As FIG. 4 shows, preamplifier 230 preferably includes two 32 channel preamplifiers, 231 and 232, corresponding to the TTU and PE/LOB transducers, respectively.

In accordance with the present invention, the nondestructive ultrasonic testing system and methods also include gate signal processing electronics coupled to the output ports of the channel switching system to receive the gate signals. Gate signal processing electronics 300 shown in FIGS. 2-4 includes a command input port 307 for receiving processing commands, and a data processing output port 308.

The gate signal processing electronics of this invention also includes means for processing the gate signals to obtain defect information. Such processing means preferably include means for finding a signal characteristic of the gate signals, such as the peak signal amplitude in a certain time window. The characteristic finding means can include gates with conventional circuitry for processing the gate signals in accordance with the TTU, LOB or PE modes. In the preferred embodiment of this invention, there is one gate for processing each gate signal. As shown in FIGS. 3 and 4, the preferred embodiment of this invention includes three TTU gates 301, two PE dual log with normalization gates 302 and 303, and LOB gate 304. The PE gates are dual gates since they compare two output signals and produce a signal (designated "NRW" in FIG. 4) which represents the difference between those signals (in other words, normalization).

As indicated previously, although a six-gate system is shown, the system configuration can be easily changed. For example, the two PE dual gates can each be software configured as two single PE gates, thus making a total of eight gates. In the system as configured in FIGS. 2-4, transducer channels 1-21 correspond to one TTU gate, transducer channels 22 and 27-32 correspond to a second TTU gate, transducer channels 23-26 correspond to a third TTU gate, transducer channels 31-34 correspond to one PE gate, transducer channels 35-38 correspond to the LOB gate, and transducer channels 39-64 correspond to the other PE gate.

Each of the gates in the preferred embodiment examines a different gate signal, shown as one of $Rf_A$-$Rf_F$ in FIG. 4, and each gate produces an output, designated $UT_{DC1}$-$UT_{DC6}$, which indicates the maximum amplitude of the corresponding gate signal during a certain time window. The occurrence of the time window reflects the mode of the gate. That time window is defined by a window signal which is preferably determined by gates 301-304 themselves and outputted from those gates. Of course, gates 301-304 could also determine another characteristic of the gate signals for other processing.

Each of the gates also receives, as one of the processing commands, a pulse command signal which corresponds to the pulse command signal sent to the channel switching system. The gates use the pulse command signal for synchronization with the remainder of the system. LOB gate also receives a thickness signal LOB.

In the preferred embodiment, each gate also outputs a logarithmic gate signal corresponding to the linear gate signals from pulse receivers 210 and 220. The logarithmic signals, denoted as $Rf_{LOG}$, afford a wider dynamic range than the linear gate signal. In the preferred embodiment, the PE/LOB gates 302-304 also output a status signal which corresponds to the width of the part proximate the corresponding transducer.

Thus, the outputs of the six gates in the preferred embodiment are six Rf linear signals, six Rf logarithmic signals, six window signals, three status signals, and ten UTDC signals (one for each TTU gate, one for the LOB gate, and three for each PE gate, i.e., two amplitude signals and the normalization signal for each PE gate).

In accordance with the present invention, the gate signal processing electronics also includes means for selecting certain of the defect information according to processing commands at the command input port, the selected defect information being sent to the data processing output port. FIGS. 3 and 4 show multiplexers 310 and 320 and gate controller 330 as such means. The outputs from gates 301-304 are inputs to those several multiplexers.

Multiplexer 320, called the "gate signal multiplexer," receives as inputs all the $UT_{DC}$ signals and produces as outputs two signals. One of the outputs is a $UT_{DC}$ signal selected from TTU gate 301, and the other output signal is a $UT_{DC}$ signal selected from PE and LOB gates 302-304. Preferably, gate signal multiplexer 320 includes analog multiplexers DG508A. The control and selection inputs to the channel signal multiplexer 320 are provided from gate controller 330.

Figure 6A:
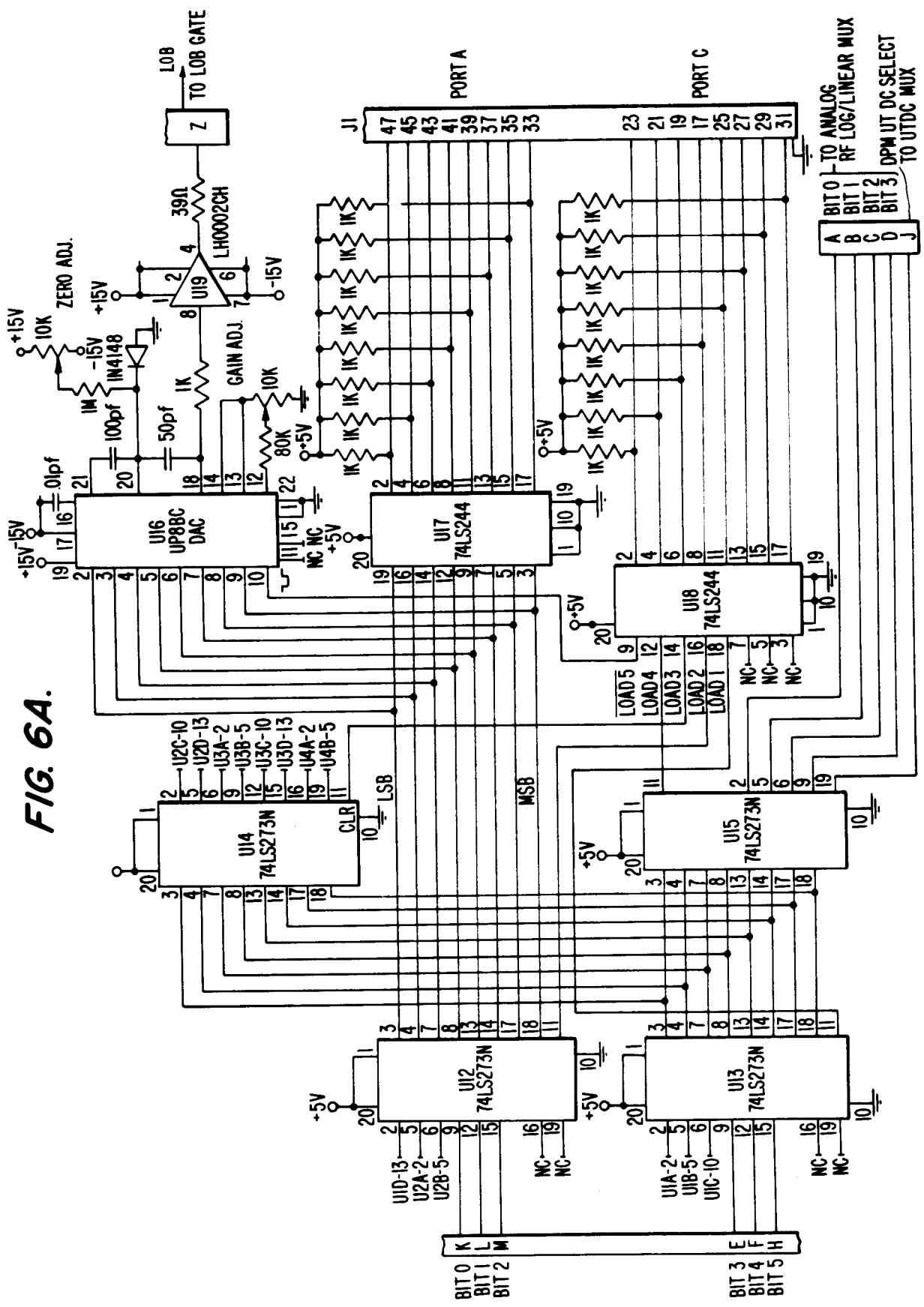
FIGS. 6A and 6B shows a circuit diagram of a gate controller shown in the system shown in FIG. 4.
Figure 6B:
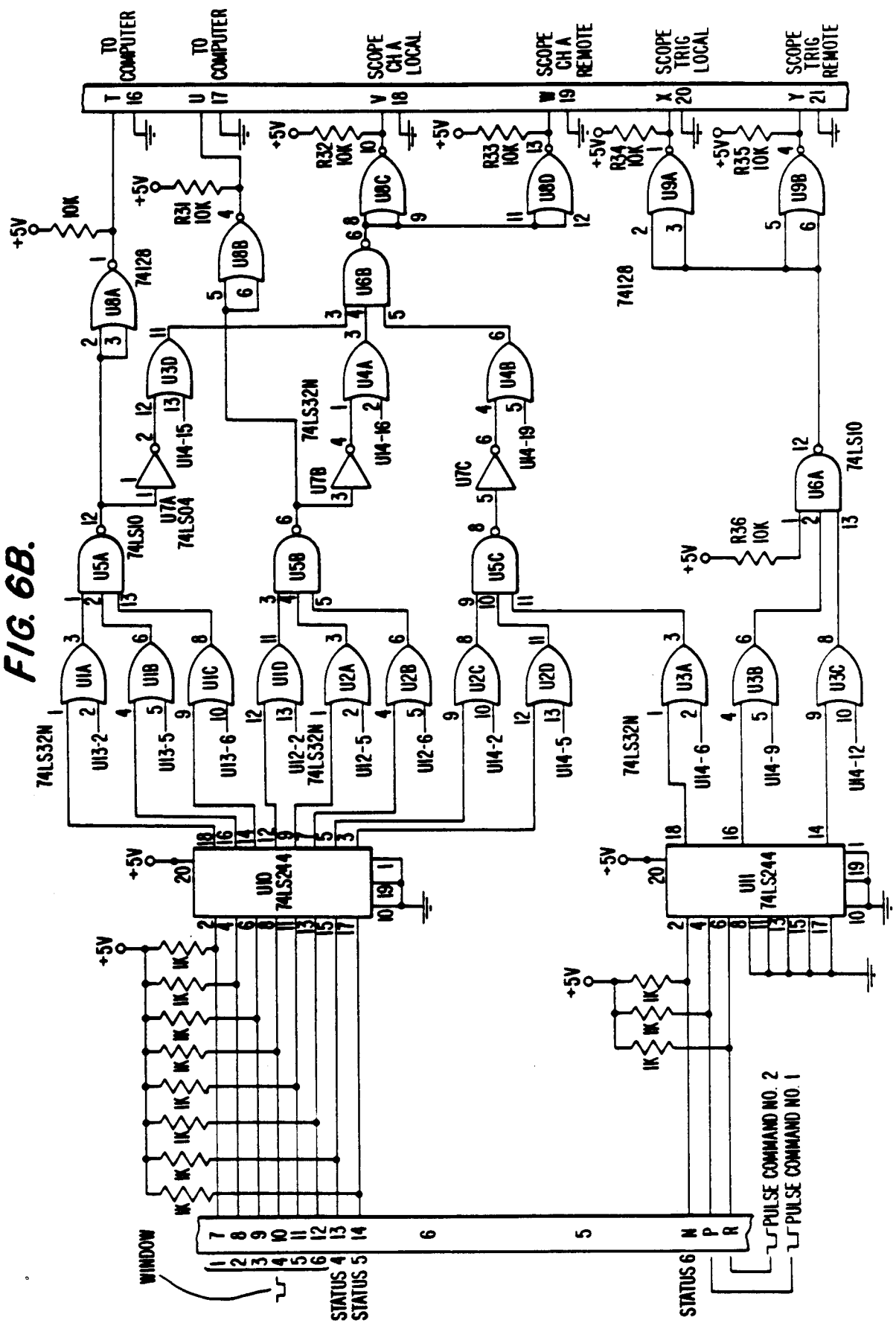

A preferred embodiment for gate controller 330 is shown in FIGS. 6A and 6B. In FIG. 6A, registers U12-U15 are octal D-type flip-flops. These registers have commonly-connected inputs and are used to store processing commands from microcomputer 400. The inputs to registers U12-U15 are also commonly connected to the input of digital-to-analog converter U16 which supplies a part thickness signal LOB to LOB gate 304.

Data at the inputs to registers U12-U16 is provided by microcomputer 400 via bus driver U17. Driver U17 is preferably part of the command signal input port 307 of the gate signal processing electronics. Microcomputer 400 also supplies control signals to elements U12-U16 via bus driver U18, which is also preferably part of command signal input port 307. The outputs of driver U18 are LOAD signals which cause elements U12-U16 to store the data at their inputs. In this manner, microcomputer 400 controls both the data input to these elements, and the actual loading of the data into the elements.

Six of the outputs from registers U12 and U13 in gate controller 330, bits 0-5, are used to control the analog multiplexers in gate signal multiplexer 320 described above.

As FIG. 4 also shows, gate controller 330 receives as inputs the window signals, status signals, and pulse command signals from gates 301-304. Gate controller 330 also outputs to data processing output port 308 and oscilloscopes 350 and 351 and certain ones of the input signals which correspond to the $UT_{DC}$ signals selected by multiplexer 320 and to the Rf signal selected by multiplexer 310 (described in detail below).

As shown in FIG. 6B, window signals 1-6 are inputs to buffer U10, as are status signals 4 and 5. Window signals 1-3 then feed an input of OR gates U1A-U1C, respectively, whose other input is a selection signal supplied from microcomputer 400 via U13. The outputs of OR gates U1A-U1C are inputs to NAND gate U5A whose output, after being inverted by NOR gate U8A, is one of the selected window singals.

The other selected window signal is from window signals 4-6 which feed a similar OR-NAND circuit comprising elements U1D, U2A, U2B, U5B, U8B as shown in FIG. 6B. The selection signal inputs to elements U1D, U2A and U2B are provided from microcomputer 400 via register U12 shown in FIG. 6A.

One of status signals 4-6 (status signal 6 being an input to buffer U11) is selected from a OR-NAND circuit comprising gates U2C, U2D, U3A and U5C. The selection signal inputs to the OR gates U2C, U2D, and U3A are provided from microcomputer 400 via register U14 of FIG. 6A. This selected status signal, as well as one of the selected window signals, feed another selection circuit which includes inverters U7A-U7C, OR gates U3D, U4A, U4B, NAND gate U6B, and NOR gates U8C and U8D. The outputs from NOR gates U8C and U8D are inputs to both a local and remote oscilloscope. The selection inputs to the OR gates U3D, U4A, and U4B are also provided from microcomputer 400 via register U14 of FIG. 6A.

As FIG. 4 shows, the preferred embodiment of this invention includes a built-in, or local, oscilloscope 350 and has the capability for a remotely-located oscilloscope, such as oscilloscope 351. Those oscilloscopes display selected Rf signals and corresponding window/status signals. The selection of the window/status signals to be displayed is as described above.

The trigger signal for oscilloscopes 350 and 351 is derived from the pulse command signals input to gate controller 330. Those pulse command signals are input to buffer U11 of FIG. 6B, and the corresponding outputs of buffer U11 are sent through a selection circuit comprising OR gates U3 and U3C and NAND gate U6A. The selection inputs to the OR gates U3B and U3C are generated from register U14, and the output of NAND gate U6A is buffered by NOR gates U9A and U9B.

Display multiplexer 310 selects the Rf inputs to the local and remote oscilloscopes 350 and 351. Multiplexer 310 receives as inputs the six Rf linear signals $Rf_{A1}$-$Rf_{F1}$, as well as the Rf logarithmic signals from gates 301-304. Display multiplexer 310 preferably also includes an analog multiplexer DG506A with selection control signals provided by microcomputer 400 via register U15, shown in FIG. 6A, from gate controller 330.

As described above, digital-to-analog converter U16, also shown in FIG. 6A, is used to send an analog signal to LOB gate 304. Preferably, converter U16 includes an internal storage register which receives data from buffer U17 when the LOAD 5 signal from buffer U18 is pulsed. The output of converter U16 is fed through buffer amplifier U19 before being outputted to LOB gate 304 as signal LOB.

As FIG. 4 also shows, a remote voltmeter 352 can also be coupled to gate signal electronics 300 to measure one of the $UT_{DC}$ signals. The $UT_{DC}$ output for the voltmeter is received from the gate multiplexer 320 which selects a $UT_{DC}$ signal either from the TTU gates or from the PE/LOB gates according to a DPM $UT_{DC}$ select signal stored in gate controller register U15 (FIG. 6).

In accordance with the present invention, the system for nondestructive ultrasonic testing includes data processing means coupled to the data processing output port of the gate signal processing electronics and to the channel switching system input ports. The data processing means generates the control signals, the pulse command signals, and processing commands, and receives and evaluates the selected defect information from the gate signals processing electronics. In the preferred embodiment shown in FIGS. 2-4, such data processing means includes microcomputer 400. The specific elements of microcomputer 400 are shown in greater detail in FIGS. 3 and 4. Those elements include central processing unit (CPU) 410, which is preferably an INTEL iSBC86/30 single board computer.

Microcomputer 400 also includes memory 415, shown in FIG. 3, which acts as a means for storing both data and programs. As FIG. 4 shows, memory 415 preferably includes an INTEL memory board iSBC012C Random Access Memory ("RAM"), and, for more permanent storage, and INTEL bubble memory board iSPC254S-4. Microcomputer 400 also includes a floppy disk 419, for example, Shugart 850 dual floppy disk drives, as well as a floppy disk controller 418, which preferably comprises an INTEL iSBC208 Flexible Disk Drive Controller.

In operation, CPU executes programs stored in memory 415 as well as disk 419, and arithmetically processes the defect signals received from the gate signal processing electronics.

In accordance with the present invention, the data processing means, which would also include input/output ("I/O") circuitry coupled to the microcomputer, also includes means for placing the defect signals into a signal format acceptable for input to the microcomputer and for generating protocol signals for input to that microcomputer. An example of such means in the present embodiment includes data acquisition electronics 426 which is shown in FIG. 4 as including elements 421 and 422. Elements 421 and 422 each contain analog-to-digital converters for placing the analog signals from multiplexer 320 into a digital format acceptable for microcomputer 400, and includes standard INTEL I/O circuitry for coordinating the input of information into microcomputer 400. Such input and storage includes use of the standard INTEL protocol signals which elements 421 and 422 also generate. The specifications for interfacing with INTEL microcomputer iSCB86/30 may be found in the Intel reference manual entitled "Guide to Multibus Interlock Circuitry," which is incorporated herein by reference.

In accordance with the present invention, the I/O circuitry of the data processing means also includes means for generating pulse command signals in response to outputs from the microcomputer. Circuitry for generating such pulse command signals is shown as elements 421a and 422a, which are part of elements 421 and 422, respectively. Preferably, elements 421a and 422a, in addition to including the necessary circuitry to interface with the microcomputer 400, also include elements such as monostable multivibrators for generating pulse commands of a predetermined duration.

Furthermore, in the preferred embodiment shown in FIGS. 3 and 4, there is a user console means 450 coupled to microcomputer 400 for allowing external control of CPU 410 both to input commands and to receive data. Preferably, such user console means includes a conventional CRT/Keyboard terminal, such as Ann Arbor Terminals CRT 24-80, which is coupled to microcomputer 400 via a standard 9600 Baud RS232 interface.

In addition, the system for nondestructive ultrasonic testing of an object may also include external processing systems coupled to the microcomputer for exchanging data and commands with the microcomputer. An example of such an external processing system is computer 480 shown in FIGS. 2 and 4. In FIG. 4, system 480 is designated as a Data General MV-4000. System 480 is also coupled to microcomputer 400 over a standard 9600 Baud RS232 rate communication line by way of a standard I/O expansion board, such as the INTEL iSBC517 board. That board would also allow connection with several TTL I/O lines. In addition, a Datel ST1-728 D/A converter 475 can be used to reconstruct analog data, such the $UT_{DC}$ signals, for input to system 480.

As is apparent from the description of the operation of the components of this system, the data processing means, for example microcomputer 400 in FIGS. 2-4, controls the different system elements to implement the purposes of the present invention. For example, the data processing means determines the time division multiplexing of the transducer channels to the gates, and the time division multiplexing of the defect information from the gates.

In the following discussion of the software used with the preferred embodiment of the present invention, the term "SBCX12" refers to signals sent to element 422 for control of PE/LOB pulser/receiver 221 and of the window and $UT_{DC}$ selection from the PE/LOB gates 302-304 by controller 330. The term "SBCX11" refers to signals sent to element 421 for control of TTU pulser/receiver 211 and of the window and $UT_{DC}$ selection of TTU gate 301 by controller 330. The term "DISP" refers to signals for the selection of signals for the oscilloscope 350 (and 351 if one is included). The term "DISPA" refers to signals for control of display multiplexer 310. The term "LOB" corresponds the LOB signal sent from gate controller 330 to LOB gate 304.

In accordance with the system of the present invention, memory 415 contains at least one table, called a channel table, having all the necessary signal information for each channel. Using the channel table allows easy modification and reconfiguration of the ultrasonic testing system and methods of this invention.

Two examples of channel tables are shown in FIGS. 7 and 8 for a sixty-four (64) channel system in accordance with this invention. For each channel 1-64, there are four corresponding columns of entries SBCX11, SBCX12, DISP, which and DISPA contain data for the purposes indicated above.

Thus, in the channel table shown in FIG. 7 the hexadecimal "06" in the channel 1 entry for SBCX11 indicates that the investigation signals from channel 1 should be evaluated by TTU gate 1. An SBCX11 entry of hexadecimal number "0D" corresponds to TTU gate 2, and an SBCX11 entry of hexadecimal "FF" means "disable," or, in other words, the channel does not correspond to the TTU gates. As is apparent, the assignment of transducer channels to corresponding gates in the TTU mode can be effected easily via software or firmware.

In the column marked SBCX12 an entry of hexadecimal "23" corresponds to one signal for dual PE gate 2, an entry of hexadecimal "06" corresponds to the LOB gate, an entry of hexadecimal "0D" corresponds to one signal for dual PE gate 1, and an entry of hexadecimal "FF" means "disable," or, in other words, the channel does not correspond to a PE or LOB gate.

In the DISP column, entries of hexadecimal "D7" refers to the window signal from TTU gate 301. The entries of hexadecimals "6E," "6B," and "6D," correspond respectively to the status signals from the LOB gate 304, the PE gate 302, and the PE gate 303.

| Signal Source | Hexadecimal entries |
|---|---|
| Rf Linear 1 | 00 |
| Rf Linear 2 | 01 |
| Rf Linear 3 | 02 |
| Rf Linear 4 | 83 |
| Rf Linear 5 | 84 |
| Rf Linear 6 | 85 |
| Rf Log 1 | 06 |
| Rf Log 2 | 07 |
| Rf Log 3 | 08 |
| Rf Log 4 | 8A |
| Rf Log 5 | 8B |
| Rf Log 6 | 8C |

FIG. 8 shows a different channel table which corresponds more closely to the configuration of the preferred embodiment discussed above.

For each transducer channel to be evaluated, the SBCX11, SPCX12, DISP, and DISPA values are sent to the gate controller shown in FIG. 6. As explained above, the SBCX11 values are loaded into U13 by a LOAD 1 pulse, the SPCX12 values are loaded into register U12 by a LOAD 2 pulse, the DISP values are loaded into register U14 by a LOAD 3 pulse, and the DISPA values are loaded into register U15 with a LOAD 4 pulse. When the LOB signal is to be sent to the LOB gate, an LOB value, which is also stored in memory, is loaded into converter U16 with a LOAD 5 pulse.

From the description of the channel table and the hardware in FIGS. 2–6, it is apparent how the time division multiplexing of the channels and gates of this invention can be effected. Computer 400 selects the channels in the order prescribed by an operator or programmer, and the necessary data for these channels is outputted to the gate signal electronics. When the testing system is changed by, for example, adding or deleting transducers or gates, or by reconfiguring the transducers or gates, all that need be done is to generate a new channel table to reflect the changes. Thus, the system and methods of this invention is very flexible.

Figure 9:
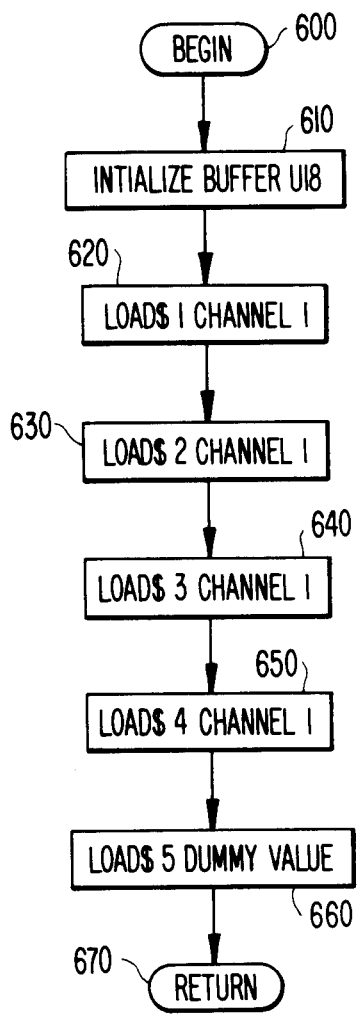

FIG. 9 shows a flow chart for a routine to initialize the gate controller in FIGS. 6A and 6B for channel 1. Step 600 corresponds to the beginning of the routine and step 610 corresponds to the initialization of buffer U18 to ensure all its outputs are at the proper level. In step 620, the LOAD$1 routine is called to load the U13 register with the values for channel 1. In step 630, the LOAD$2 routine is called to load register U12 with the corresponding SBCX12 values for channel 1. In step 640, the LOAD$3 routine is called to load U14 with the DISP values for channel 1, and in step 650, the LOAD$4 routine is called to load register U15 with the DISPA values for channel 1. Steps 660 represents a call to the LOAD $15 routine to place a dummy value into converter U16. The procedures is ended with the return 670.

Figure 10:
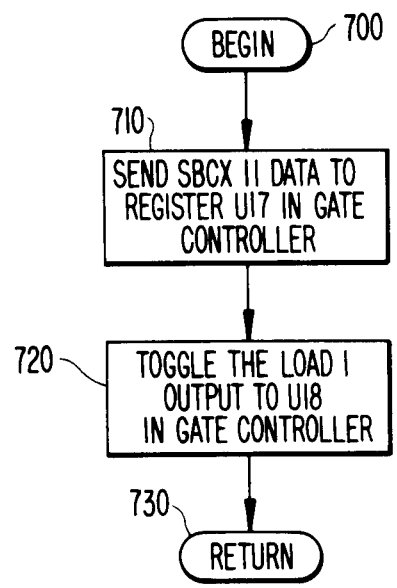
Figure 11:
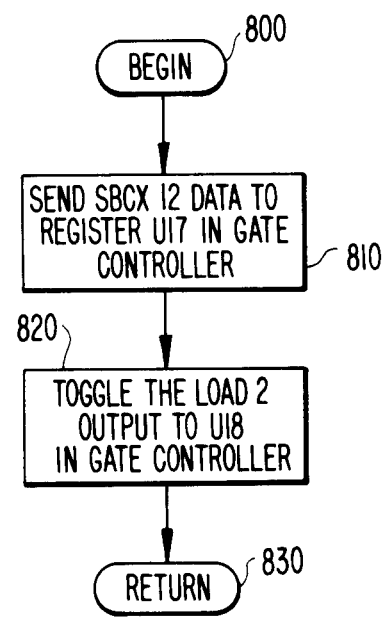

FIGS. 10–14 represent the procedures for the LOAD$1–LOAD$5 routines, respectively. Only the LOAD$1 routine in FIG. 10 will be described in any detail because of the similarity of the steps in the flow chart. In FIG. 10, the routine begins with the entry at step 700, and in step 710, the data output SBCX11 of the corresponding channel is output to the U17 bus driver in gate controller 330. In step 720, the LOAD 1 signal, which is an input to bus driver U18, is toggled by first switching the output to one state and then to the other state after a predetermined time. Toggling the LOAD1 signal loads the U13 register with information output through bus driver U17. Step 730 is the return step. The LOAD$2–LOAD$5 routines each have steps corresponding to steps 700–730 which perform in a similar manner.

Figure 15:
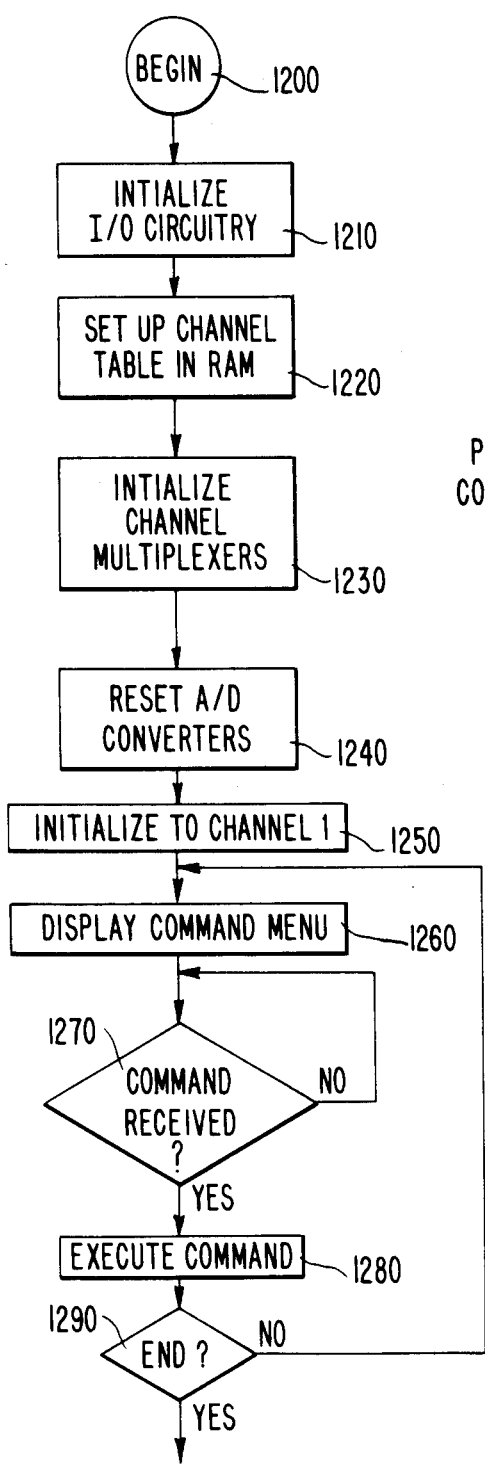
FIG. 15 is a flow chart for operation of the entire system and method of this invention.

FIG. 15 shows a flow chart for the normal operation of the system and methods of this invention. After beginning in step 1200, the input/output circuitry is initialized in step 1210. Such input/output circuitry typically includes elements 421, 422 and 470 shown in FIG. 4. In the initialization the appropriate signals are sent to the hardware, after power is supplied to those elements, to ensure that the outputs are in a known state.

In step 1220, the channel table is initialized in the RAM. The channel table, such as in FIGS. 7 or 8, can either be read from disk 419, inputted via terminal 450 or remote processor 480, or preprogrammed via firmware in a portion of the memory.

The next step, step 1230, initializes the channel multiplexers. This involves sending control signals to pulser/receivers 210 and 220 so that they will instruct multiplexers 212 and 222 to select the initial transducer channel signals as gate signals.

In step 1240, the A/D converters are reset. This is a clearing operation which removes any built-up charge from the input of the converters. This initialization typically involves shorting out a transistor switch at the input to the A/D converters.

In step 1250, the information for channel 1 is sent to registers U12–U16 by the method explained with regard to FIG. 9. Then, a command menu is displaced at terminal 450, step 1260. When a command is received as determined by step 1270, the command is executed at step 1280. If a procedure is not at an end, then the command menu in step 1260 is redisplayed.

The preferred embodiment of the system of this invention includes many commands not necessary to an understanding of the operation of this system. Those commands of interest for operation includes M, 6, r, &, 9, ), +, −, H, ctl C The "M" command gives remote control to the processor 480. The 6 command followed by a channel number displays that channel on the oscilloscopes and scans that channel 1,000 times, and the "r" command followed by a channel number displays that channel on the oscilloscope and scans it 65,000 times. The "&" command followed by a channel number displays that channel on the oscilloscope and scans that channel forever (or until a "ctl C" command). A "ctl C" (Control C) command stops the current operation.

The "9" command scans the blade side channels once, the ) command scans the tool side channels once, the "+" command scans the blade side channels continuously until a "ctl C" command is received and the "−" command scans the tool side channels continuously (or until a "ctl C" command is received. The blade side and tool side channels are defined in the software.

The "H" command is a Help command which assists the user in operating the system.

Commands of interest for debugging include:

2, 3, #, 4, ", 5, %, 8

The "2" command strobes the pulse command and pulser/receivers 210 and 220 continuously until a "ctl C" command is received. The "3" command, followed by a channel number, scans that channel once. .The "#" command followed by a channel number scans that channel continuously until a "ctl C" is received. The "4" command toggles the multiplexes continuously until a "ctl C" command is received. The command strobes the pulse command on pulse receivers 210 and 220 continuously until a "ctl C" command is received.

The "5" command followed by a channel number displays that channel on the remote and local oscilloscopes, and the "%" command followed by a channel number performs the same operation but also strobes the pulse command of pulse/receiver 210 and 220. The "8" command ,initializes the gate controller continuously until a "ctl C" is received.

Persons of ordinary skill in the art will be able to develop or adapt existing software to implement the commands in accordance with the preferred embodiment of this invention, especially using the channel table described herein. As can be seen, the system and method of this invention allows time division multimplexing of signals, as well as easy system reconfiguration, using software tables in memory.

It will be apparent to those skilled in the art that modifications and variations can be made in the nondestructive ultrasonic testing methods and apparatus of this invention. The invention in its broader aspects is not limited to the specific details, representations, methods and apparatus, and illustrative examples shown and described above. Departure may be made from such details without departing from the spirit of scope of the general inventive concept.

What is claimed is:

1. A system for nondestructive ultrasonic testing of an object comprising:
    (a) a plurality of transducer systems positioned proximate said object to transmit ultrasonic energy toward said object in response to activation signals, to receive ultrasonic energy from said object, and to create investigation signals from said received ultrasonic energy;
    (b) a channel switching system coupled to said transducer systems to receive said investigation signals from said transducer systems and to output said activation signals to said transducer systems, said channel switching system including:
        (i) a set of input ports receiving pulse command and control signals,
        (ii) a set of output ports containing gate signals,
        (iii) means, coupled to said input ports and to said transducer systems, for transforming said pulse command signals at said input ports into activation signals to drive said transducer systems, and
        (iv) means, coupled to said transducer systems and to said output ports, for selecting, in accordance with said control signals, certain ones of said investigation signals from said transducer systems to be gate signals, and for routing said gate signals to said output ports;
    (c) gate signal processing electronics coupled to said output ports of said channel switching system to receive said gate signals, said gate signal processing electronics having a command input port for receiving processing commands and a data processing output port and including
        (i) means for processing said gate signals to obtain defect information, and
        (ii) means for selecting certain of said defect information according to said processing commands at said command input port, said selected defect information being sent to said data processing output port; and
    (d) data processing means, coupled to said data processing output port, to said command input port, and to said channel switching system input ports, for generating said control signals, pulse command signals, and processing commands, and for receiving and evaluating said selected defect information.

2. The system in claim 1 wherein said selecting means of said channel switching system includes a channel multiplexer responsive to said control signals, with inputs coupled to receive said investigation signals and outputs coupled to said output ports.

3. The system in claim 2 wherein said channel switching system also includes means for amplifying said investigation signals before said investigation signals are inputted to said channel multiplexer.

4. The system in claim 1 further including high voltage inputs and wherein said transforming means of said channel switching system includes signal buffers coupled to said high voltage inputs.

5. The system of claim 1 wherein said gate signal processing means of said gate signal processing electronics includes means for processing said gate signals in a TTU mode.

6. The system of claim 1 wherein said gate signal processing means of said gate signal processing electronics includes means for processing said gate signals in a PE mode.

7. The system of claim 1 wherein said gate signal processing means of said gate signal processing electronics includes means for processing said gate signals in an LOB mode.

8. The system of claim 1 wherein said gate signal processing means of said gate processing electronics includes means for finding a signal characteristic of said gate signals.

9. The system of claim 8 wherein said signal characteristic finding means includes
    means for determining desired time windows; and
    means for finding peak signal values of said gate signals within said desired time windows.

10. The switching system of claim 8 wherein said selecting means of said gate signal processing electronics includes a gate signal multiplexer coupled to said signal characteristic finding means, said gate signal multiplexer being controlled according to said processing commands.

11. The system of claim 1 further including an oscilloscope display coupled to said gate signal processing electronics.

12. The system of claim 11 further including a display multiplexer coupled to said gate signals and being controlled according to said processing commands, said display multiplexer having an output coupled to said oscilloscope display.

13. The system of claim 12 wherein said gate signal processing electronics coupled to receive said processing commands, further includes a gate controller said gate controller including means for controlling said display multiplexer according to said processing commands; and means for a synchronizing said oscilloscope display with said gate signal.

14. The system of claim 13 wherein said gate controller includes registers for storing selection information according to said procesing command, and wherein said display multiplexer includes means for choosing one of said gate signals for said oscilloscope display according to said selection information.

15. The system of claim 13 wherein said gate controller includes registers for storing selection information according to said processing commands, wherein said signal characteristic finding means includes outputs representing said signal characteristic, and wherein said gate signal multiplexer includes means for choosing an output of said signal characteristic finding means according to said selection information.

16. The system of claim 1 wherein said data processing means includes:

a microcomputer including means for storing programs for controlling said ultrasonic testing system, and means for executing programs stored in said storing means and for arithmetically processing said defect signals; and I/O circuitry coupled to said microcomputer, said I/O circuitry including means coupled to said data processing output ports of said gate signal processing electronics for converting said defect signals into a signal format acceptable for input to said microcomputer and for generating protocol signals for input to said microcomputer, and means for generating said pulse command signals in response to outputs from said microcomputer.

17. The system of claim 16 further including user console means, coupled to said microcomputer, for receiving commands for external control of said programs executing means.

18. The system of claim 16 further including an external processing system coupled to said microcomputer for exchanging data and commands with said microcomputer.

19. A method of nondestructive ultrasonic testing of an object including the steps of:

sending ultrasonic energy to and receiving ultrasonic energy from said object;

transducing said received ultrasonic energy to form investigation signals;

selecting certain of said investigation signals to be gate signals;

processing said gate signals to obtain defect information; and selecting certain of said defect information for subsequent processing.

20. The method of claim 19 wherein said selecting steps each include the step of selecting according to a prescribed order to effec time division multiplexing.

21. The method of claim 19 wherein said channel signal selecting step includes the steps of:

inputting a series of steps to a data processor; and interpreting said steps to effect channel signal selection.

22. The method of claim 19 wherein said defect information selecting step includes the steps of:

inputting a series of steps to a data processor; and interpreting said steps to effect defect information selection.

* * * * *

UNITED STATES PATENT AND TRADEMARK OFFICE
CERTIFICATE OF CORRECTION

PATENT NO. : 4,799,167  
DATED : January 17, 1989  
INVENTOR(S) : Dennis P. Sarr It is certified that error appears in the above-identified patent and that said Letters Patent is hereby corrected as shown below:

In the title, change "ULTROSONIC 64 CHANNEL INSPECTION SYSTEM WITH MULTIGATE/MULTIMODE SELECTION SOFTWARE CONFIGURABILITY" to --ULTRONSONIC 64 CHANNEL INSPECTION SYSTEM WITH MULTIGATE/MULTIMODE SELECTION SOFTWARE CONFIGURABILITY, WITH SOLID STATE ELECTRONICS FOR HIGH RELIABILITY--.

Claim 9, line 50, change " means for determining desired time windows; and" to --means for designating predetermined periods of time within the duration of said investigation signals as desired time windows; and--.

Claim 13, line 1, change " includes a gate controller said" to --includes a gate controller, said--.

UNITED STATES PATENT AND TRADEMARK OFFICE
CERTIFICATE OF CORRECTION

PATENT NO. : 4,799,167
DATED : January 17, 1989
INVENTOR(S) : Dennis P. Sarr

It is certified that error appears in the above-identified patent and that said Letters Patent is hereby corrected as shown below:

Claim 20, line 27, change "effec" to --effect--.

Signed and Sealed this

Thirtieth Day of January, 1990

Attest:

JEFFREY M. SAMUELS

*Attesting Officer*     Acting Commissioner of Patents and Trademarks